(12) United States Patent
Flock et al.

(10) Patent No.: US 6,352,517 B1
(45) Date of Patent: Mar. 5, 2002

(54) OPTICAL MONITOR OF ANATOMICAL MOVEMENT AND USES THEREOF

(76) Inventors: Stephen Thomas Flock, 33 Ledgelawn Dr., Little Rock, AR (US) 72212; Kevin Scott Marchitto, 14708 Ridgewood Dr., Little Rock, AR (US) 72211

( * ) Notice: Subject to any disclaimer, the term of this patent is extended or adjusted under 35 U.S.C. 154(b) by 0 days.

(21) Appl. No.: 09/321,323

(22) Filed: May 27, 1999

Related U.S. Application Data

(60) Provisional application No. 60/087,713, filed on Jun. 2, 1998.

(51) Int. Cl.$^7$ .................................................. A61B 5/00
(52) U.S. Cl. ........................................ 600/595; 600/558
(58) Field of Search ................................ 600/529, 534, 600/587, 558, 595

(56) References Cited

U.S. PATENT DOCUMENTS

| | | | | |
|---|---|---|---|---|
| 4,859,181 A | * | 8/1989 | Neumeyer | |
| 5,073,706 A | * | 12/1991 | Kulju | |
| 5,265,609 A | * | 11/1993 | Buchanan et al. | |
| 5,505,199 A | * | 4/1996 | Kim | |
| 5,551,879 A | * | 9/1996 | Raynie et al. | |

* cited by examiner

*Primary Examiner*—Max Hindenburg
(74) *Attorney, Agent, or Firm*—Benjamin Aaron Adler

(57) ABSTRACT

The present invention provides an apparatus and means for non-invasively measuring the real time movement of external or internal body parts, thereby improving the diagnosis of, for example, respiratory disease and the monitoring of therapy.

15 Claims, 4 Drawing Sheets

OPTICAL MONITOR OF ANATOMICAL MOVEMENT AND USES THEREOF

CROSS-REFERENCE TO RELATED APPLICATION

This patent application claims benefit of provisional patent application U.S. Serial No. 60/087,713, filed Jun. 2, 1998, now abandoned.

BACKGROUND OF THE INVENTION

1. Field of the Invention

The present invention relates generally to the fields of optical imaging and medical diagnosis. More specifically, the present invention relates to an apparatus and means for non-invasively measuring the movement of various parts of the human body, most notably thoracoabdominal movement associated with breathing.

2. Description of the Related Art

There are a variety of conditions whereby unambiguous, quantitative measurements of the movement of human anatomical structures would be of diagnostic benefit. For example, the presence and magnitude of hand tremor is associated with certain neurologic and muscular disease processes. Specific parameters of rapid e y e motion (REM) during certain phases of sleep is diagnostic of some abnormal conditions. The rate and relative movement of the thorax that is associated with breathing also provides potentially important diagnostic information, such as presence of asthma or other respiratory diseases, airway blockage, or other abnormal lung function.

The societal and financial cost to health care infrastructure and the economy as a whole as a consequence of respiratory disease is immense. Newacheck and Halfon (1) determined that approximately 6.5% of all children in the United States, experienced some degree of disability, with the most common causes of being respiratory diseases and mental impairments. This results 24 million days lost from school and in an added 26 million physician contacts and 5 million hospital days annually. In an earlier study (2), investigators found that the prevalence of asthma in children younger than 18 years of age in the United States was 4.3% in 1988 and was 3.2% in 1981 resulting in 12.9 million contacts with medical doctors, and 200,000 hospitalizations. The 10% of children with severe asthma accounted for 35% of hospitalizations and 77% of the days in the hospital. Chronic conditions such as asthma result in a huge burden to the economy of the United States. In fact, more than 90 million Americans live with chronic conditions (1, 2), which include diabetes and heart disease as well as asthma. Respiratory disease accounts for, or is associated with, as much as 10% of chronic disease, resulting in healthcare costs in excess of $65 billion annually.

Respiratory disease is the number one cause of morbidity and mortality in infants worldwide. Measurements of lung function (e.g. tidal volume, $V_T$, which is the volume change from the peak expiration volume to the minimum inspiration volume) give insight into the respiratory status of humans. Other breathing indices give further clinical information; for example, the time to peak expiratory volume ($t_{PTEF}$) combined with total expiratory time ($t_E$) provides information on airway caliber. Respiratory frequency, $f_R$, is the most utilized variable of breathing pattern in clinical practice, and provides diagnostic information on cardiorespiratory and systemic disease, pneumonia, sepsis, congestive heart failure, etc. Thoracoabdominal asynchrony in movement also provides important clinical information, especially in infants.

In infants and children, measurement of $V_T$ is usually done with a pneumotachygraph (PNT), which involves attaching a facemask to the infant. This method causes subject anxiety and results in a transient, but long-lived increase in $f_R$ and decrease in $V_T$. In fact, simply touching the infant results in stress, causing significant changes in many physiologic parameters. A non-contact means of measuring lung function would eliminate stress associated with manipulation of the patient while measuring respiratory function, and, therefore would provide data of greater clinical relevance.

Quantification of chest wall movement has long been regarded as clinically useful for measurements of amplitude, thoracoabdominal asynchrony, frequency, etc. In 1993, the Joint Official Statement by the American Thoracic Society and the European Respiratory Society on Respiratory Mechanics in Infants stated, " . . . little is known about the infant chest wall . . . chest wall mechanics should be studied in infants with neuromuscular disease, chest wall abnormalities, and primary lung disease, and the role of chest wall instability in overall respiratory pump malfunction should be assessed . . . chest wall motion should be investigated as an indicator of control of breathing."

Techniques to measure the motions of anatomic structures often make use of accelerometers or other mechanical transducers. The disadvantages with using these devices are their inherently low spatial resolution, extensive calibration procedures, and most of these devices must be operated in a contact mode. Mechanical arms and such that are in contact with the anatomic structure and have rotation and displacement transducers can b e used to measure movement, but these devices are cumbersome and require contact between the device and subject.

Other techniques to measure motions make use of rangefinders. For example, single lens reflex cameras use contrast maximization of an image to determine range. Ultrasound pulses and time-of-flight measurements are also used to detect motion as are changes in magnetic field strength which can further be used to determine the location of sensors. Another type of rangefinder involves projecting a pattern on the object in question, imaging the pattern shape and changes with time, and then calculating movement.

Because of the importance of being able to measure specifically the movement of the chest and abdomen, considerable effort has been expended to develop good methodologies and devices. For example, strain gauges, incorporated in straps positioned around a partial circumference of the infant, stretches during breathing, thus producing an electrical signal which can b e monitored. This method has limitations in that placement of the strap alters the readings, and the strap itself changes the compliance of the chest and abdomen thus affecting the reading. Magnetometers and changes in impedance have also been used with various degrees of success. All of these methods suffer from being unable to detect spatial non-uniformity in thoracoabdominal movement.

Since 1985, the respiratory inductive plethysmograph (RIP) has been the most commonly used monitor of thoracoabdominal movement. This device makes use of changes in inductance due to movement of coils of wire incorporated into cloth bands placed on the rib cage and abdomen. This technique is based on the determination that the total volume changes upon respiration are equal to the sum of the volume changes in the ribcage and abdomen. While the respiratory inductive plethysmograph has proven to be useful, it is difficult to calibrate, inconsistent with simultaneous measurements using strain gauges and magnetometers, and furthermore still involves disturbing the infant by the placement of the transducers on the chest and abdomen.

Several groups have investigated optical means in an effort to develop a non-contact way of monitoring thoracoabdominal movement. Laser speckle interferometry has been documented and a method based on quantifying the alteration of a pattern of markers projected on the chest has been tested. (3, 4). Aubert, et al., (5) and more recently a group in Australia (6) have tested the idea of using an optical rangefinder to monitor chest wall movement. Aubert et al. measured chest wall movements associated with the heartbeat, which were between 0.3 and 0.8 mm. Torsten et al. showed that measurements of $V_T$ and abdominal wall displacement correlated well with an independent measurement of end-expiratory lung volume. In both of these cases, ambiguity as a consequence of measuring a single point was problematic, and the use of the device in ambient lighting also presented a further complication.

None of the optical methods for measuring lung function have made the transition from the laboratory to an FDA approved clinical device. Note, however, that Cala and co-workers (7) very accurately determined lung volumes by optical reflectance motion analysis whereby 86 reflective markers were positioned on subjects and were imaged by video cameras. Based on geometric considerations, and using a surface triangulation method for volume calculations, they clearly showed that it was possible to accurately (<2% error) determine tidal volume; no calibration factor was required to correlate these data to spirometer readings.

The prior art is deficient in the lack of an optical apparatus and effective means for measuring the movement of anatomical structure non-invasively, especially for measuring thoracoabdominal movement associated with breathing. The present invention fulfills this long-standing need and desire in the art.

SUMMARY OF THE INVENTION

The present invention is directed to an apparatus and means for non-invasively measuring the real time movement of external or internal body parts, thereby improving the diagnosis of, for example, respiratory disease and the monitoring of therapy. The apparatus is inexpensive, portable, non-contact, simple to use, and can be configured to work through an endoscope.

In one embodiment of the present invention, there is provided a method for measuring body movement of a tissue of interest, comprising the steps of emitting radiant energy to the surface of the tissue to form a spot; detecting an image of the pattern of radiant energy reflected from the spot, wherein the pattern corresponds to the position of the spot relative to the source of the radiant energy; and determining the pattern change with time, wherein the pattern change corresponds to the change of the spot position relative to the source of radiant energy, thereby indicating the body movement of the tissue.

In another embodiment of the present invention, there is provided an apparatus for detecting movement of an anatomical structure, comprising a source of radiant energy; a means for projecting the radiant energy in a pattern over a region of interest in the anatomical structure and a means for detecting change in the pattern of radiant energy reflected from the region of interest. Such apparatus can be used for monitoring sudden infant death syndrome (SIDS), evaluating rapid-eye-movement (REM) sleep and other clinical purposes.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Figure 1:
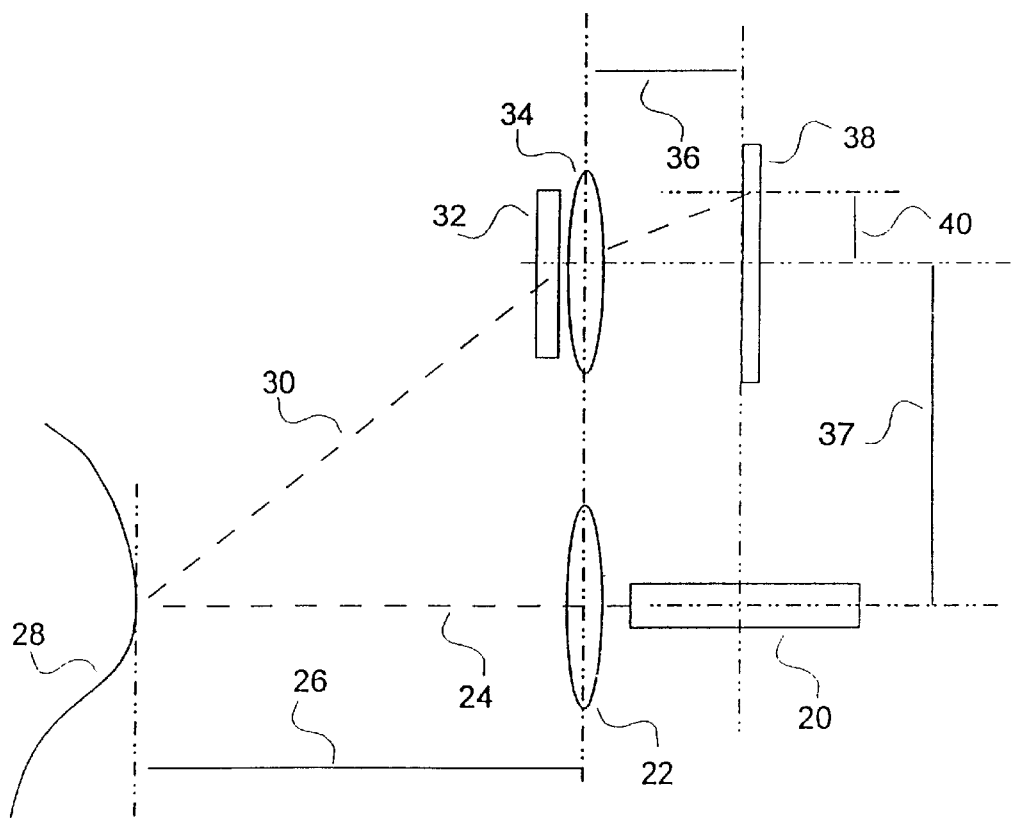
FIG. 1 is a diagram of the optical arrangment to measure the motion of an anatomical object at a single point, comprising a source of illumination 20, focused or collimated by an optic 22 to produce a beam 24 which impinges on the region-of-interest (ROI) 28. The image 30 propagates though a bandpass filter 32 and is focused with an optic 34 onto a position-sensitive-detector (PSD) 38. The distance 36, of the position-sensitive-detector from the lens is the focal length of the lens. The position 40, of the image of the spot on the position-sensitive-detector is related to the distance 26, of the output optic 22 from the region-of-interest, the distance 37, of the output optic 22 from the imaging optic 34, and the focal length 36 of the imaging optic. Alternatively, the change in distance 26 can be determined from the position 40 of the image of the spot on the position-sensitive-detector, the distance 37 between the optics and the angle between the incident radiant energy 24 and the imaged radiant energy 30.

In the present invention, the following terms have the definitions set below.

As used herein, "position-sensitive detector" shall refer to an electronic detector of radiant energy from which it is possible to determine the exact location on the detector where a particular image, such as that of a spot, impinges.

As used herein, "charge-coupled device" and "bandpass filter" shall refer to the standard definitions used by people skilled in the art of optics and/or biomedical optics.

The present invention provides a source of radiant energy and a position-sensitive detector. The source of radiant energy is a laser diode emitting radiant energy at a wavelength of 675 nm model CQL800/D; available from ThorLabs, Inc., Newton, N.J. and with a power of 5 mW. Alternatively, the laser used is a semiconductor continuous-wave device emitting no more than 5 mW of radiant energy with a wavelength of 1.55 microns (which is generally considered "eye safe") and is available from Phillips Optoelectronics, Inc. The diode was driven by a constant power diode laser driver Model EK1101; available from ThorLabs, Inc. The output of the diode is focussed to a small spot about 2×2 mm at a distance of 100 cm from the diode. The detector component consists of a one-dimensional position-sensitive detector, or position-sensitive-detector Model S1352, the output of which is conditioned by a signal processing circuit Model C3683-01, both available from Hamamatsu Corporation, Bridgewater, N.J. The output of the signal processing circuit was captured by an custom-made active consisting of resistors, capacitors and an operational amplifier low-pass filter with a cut-off frequency of about 5 Hz, which is the highest respiration rate expected to be measured with this device. The output of the active filter was captured and analyzed with an analog-to-digital ADC converter board operationg at a 50 Hz sampling rate and LabView software National Instruments, Inc., Austin, Tex. The ADC was further connected to a DOS type microcomputer. The distance between the output of the laser diode i.e. laser beam and the middle of a 100 mm focal length focusing lens positioned 100 mm in front of the PSD was 75 mm. An optical bandpass filter with 665 nm center wavelength and 30 nm full-width-half-maximum bandpass Omega Optical, Inc., Brattleboro, Vt. was positioned in front of the focusing lens in order to eliminate most of the background illumination. All optical components of the device were mounted on standard optical mounting components available from, for example, ThorLabs, Inc.

The device was tested by focusing the laser beam to a point on an 80% gray card affixed to a micrometer stage. The stage allowed for micron accuracy calibrated movement of the card in a direction parallel to the incident laser beam. Using the equations provided by Hamamatsu Corp. in their position-sensitive-detector data sheets, it was possible to convert the changing position of the image of the laser spot on the position-sensitive-detector measured in the form of current with milliamp levels to the changing distance of the card from the focusing optic knowing the distance between the focusing optic and laser beam, 75 mm, and the initial distance of the focusing optic from the grey card 200 mm. From this it was determined that the device behaved linearly over a 10 cm displacement of the grey card and it was possible to determine the change in the movement of the card to a resolution of a few microns.

The present invention is directed to an apparatus and means for non-invasively measuring the real time movement of external or internal body parts.

In one embodiment of the present invention, there is provided a method for measuring body movement of a tissue of interest, comprising the steps of emitting radiant energy to the surface of the tissue to form a spot; detecting an image of the pattern of radiant energy reflected from the spot, wherein the pattern corresponds to the position of the spot relative to the source of the radiant energy; and determining the pattern change with time, wherein the pattern change corresponds to the change of the spot position relative to the source of radiant energy, which indicates the body movement of the tissue. Preferably, the radiant energy is produced by a source such as an incandescent light source, a fluorescent light source, a light-emitting diode, and a laser. Furthermore, the reflected radiant energy may be detected by a device selected from the group consisting of a position-sensitive detector, a charge-coupled device and a photodiode detector accompanied by a reflective or transmissive mask. Representative tissues which may examined using this method include the chest wall, lung, thorax, abdomen and eyes.

In another embodiment of the present invention, there is provided an apparatus for detecting movement of an anatomical structure, comprising a source of radiant energy; a means for projecting the radiant energy in a pattern over a region of interest in the anatomical structure and a means for detecting change in the pattern of radiant energy reflected from the region of interest. Preferably, the source of radiant energy is selected from the group consisting of an incandescent light source, a fluorescent light source, a light-emitting diode, and a laser. Still preferably, the anatomical structure is selected from the group consisting of chest wall, lung, thorax, abdomen and eyes. Further preferably, pattern is generated by a scanning device selected from the group consisting of scanning mirrors and electro-optical devices. A representative example of electro-optical device is a photoacoustic deflector. The resulting generated pattern of radiant energy is composed of single or multiple spots. Representative means for detecting the pattern change include a position-sensitive detector, a charge-coupled device and a photodiode detector accompanied by a reflective or transmissive mask.

The present invention also provides a method of monitoring sudden infant death syndrome (SIDS) in an individual by attaching the apparatus disclosed herewith to the individual; and then monitoring the movement of the individual by detecting the change in the pattern of radiant energy reflected from the individual, wherein the movement reversely corresponds to the possibility of having a sudden infant death in the individual.

The present invention further provides a method of evaluating rapid-eye-movement (REM) sleep in an individual in need of such evaluation by attaching the apparatus disclosed herewith to the individual; and then monitoring the movement in the eyelids of the individual by detecting the change in the pattern of radiant energy reflected from the eyelids, wherein the movement indicates the quality of REM sleep in the individual.

The following examples are given for the purpose of illustrating various embodiments of the invention and are not meant to limit the present invention in any fashion.

EXAMPLE 1

Basic Optical Arrangement for Measuring Movement of an Anatomical Object

The basic arrangement to perform a measurement of the movement of a region of the body is shown in FIG. 1. The radiant energy output of a source of illumination 20, preferably a diode laser, is focused or collimated by an optic 22 to produce a beam 24 which impinges on the region of the body of interest 28, preferably in the shape of a small spot a millimeter across. Optionally, in order to increase the intensity of the reflected signal, it might be beneficial to affix to the anatomical object a target which has reflective microbeads, such as available from 3M, Inc. and is sometimes incorporated in the reflective markings on jogging shoes, or a retroreflective grating on the backs of automobiles. The image of the spot propagates 30 though a bandpass filter 32 and is focused with an optic 34 onto a position-sensitive-detector 36. The distance of the position-sensitive-detector from the lens is the focal length of the lens, 100 mm for example. The position 40, of the image of the spot on the position-sensitive-detector is related to the distance 26, of the output optic 22 from the region-of-interest, the distance 37, of the output optic 22 from the imaging optic 34, and the focal length 36 of the imaging optic. Alternatively, the change in distance 26 can be determined from the position 40 of the image of the spot on the position-sensitive-detector, the distance 37 between the optics and the angle between the incident radiant energy 24 and the imaged radiant energy 30.

The mechanism of the arrangement for measuring movement of an anatomical object is as follows: first, a laser projects a spot on the skin; secondly, the image of the laser spot on the skin is captured by an optical system with a position-sensitive-detector (PSD), placed behind the optical system at the focal length 36. The distance between the focusing optics and laser, 37, is known and fixed; thirdly, the (current) output of the PSD is monitored by a signal processing circuit, the output of which is captured and digitized by an analog-to-digital converter; and fourthly, the PSD output can be used to determine the distance of the image of the spot from the center of the PSD, 40. The distance to the object from the source, 26, equals to $(1/40) \times 36 \times 37$. Thus, a change in distance to the region of interest, $\Delta 26$, will result in a change in the position of the image of the spot on the PSD, $\Delta 40$, therefore changing the output of the PSD signal processing circuit.

EXAMPLE 2

Simultaneous Usage of Multiple Devices

The same arrangment is used as described above in Example 1, except multiple devices are simultaneously used. For example, for chest wall measurements, which can be used to monitor respiratory events, it would be beneficial to simultaneously interrogate three discrete locations, one on the termination of the sternum, one on the chest and one on the abdomen. The interrogating light sources could be lasers emitting at different wavelenghts, or could be broadband light sources filters with bandpass filters at three different center wavelengths. By positioning appropriate bandpass filters in front of each of the three detectors, discrimination of each interrogating light source is possible.

EXAMPLE 3

Replacement of PSD with a Reflective or Transmissive Mask and a Photodiode Detector In order to simplify the engineering of the instrument and to lower cost by avoiding the use of a position-sensitive-detector or charge-coupled device (CCD), it might be beneficial to use a similar setup as discussed in Example 1, but to employ a reflective or transmissive mask positioned between the spot of illumination in the region-of-interest and detector, whereby the mask's reflection or transmission is a function of where the imaged spot hits the mask. The light that is reflected or transmitted could then be measured with a standard, inexpensive photodiode detector instead of the more expensive position-sensitive-detectors or imaging detectors. If an "eye-safe" laser is used, the detector is a room-temperature InGaAs photodiode or CCD camera sensitive to 1.55 micron radiant energy (e.g. available from Sensors Unlimited, Inc.). Using the same geometric arguments as already discussed, absolute measurements of movement could be obtained.

EXAMPLE 4

An Arrangement with a Two-Dimensional PSD

The same arrangment is used as described in Example 1, except that a two-dimensional position-sensitive-detector is used. This eliminates any problems associated with misalignment of the illumination and detection optics, and also allows for measurements over a two-dimensional region-of-interest on the body part.

EXAMPLE 5

Replacement of PSD with a Charge-Coupled Device (CCD)

The same arrangment is used as described in Example 1, except a charge-coupled device detector is used in place of the PSD. A video camera with imaging optics is connected to the universal serial bus USB or parallel port of a microcomputer if the signal is digital, or to the analog input of an ADC is the signal is analog. The image impinging on the charge-coupled device array is outputted pixel-by-pixel in a serial fashion. Software, such as can be written in C, can be used to capture the incoming data from the CCD array. The pixels on which the image of the laser spot impinges is apparent as the reading obtained during the data collection is very much larger than the surrounding unilluminated pixels. Using the same geometric arguements as used with the position-sensitive-detector, it is then possible to determine the change in the distance between the detector and body part. The benefit of using a CCD detector as compared to a position-sensitive-detector is that the former is less expensive, more sensitive, and can provide information at video 30 Hz rates or faster. Furthermore, the charge-coupled device can also be used to capture a regular video image of the body part being interrogated.

EXAMPLE 6

An Arrangement with the Output Modulated

The same arrangements as discussed in the above Examples are used, except that the output of the laser diode is modulated by a waveform produced by a digital-to-analog DAC board incorporated within the microcomputer, and the detector is monitored by a lock-in amplifier, the reference frequency of which is the same as that which modulates the laser diode. The output of the lock-in amplifier is monitored by an ADC board within the microcomputer. The benefit of this arrangment is that if the modulation is done at a frequency other than the line frequency 60 Hz, or multiples or sub-multiples of it, then ambient light can be discriminated against in the measurement.

EXAMPLE 7

An Arrangement to Measure Chest Wall and Lung Volume

Figure 2:
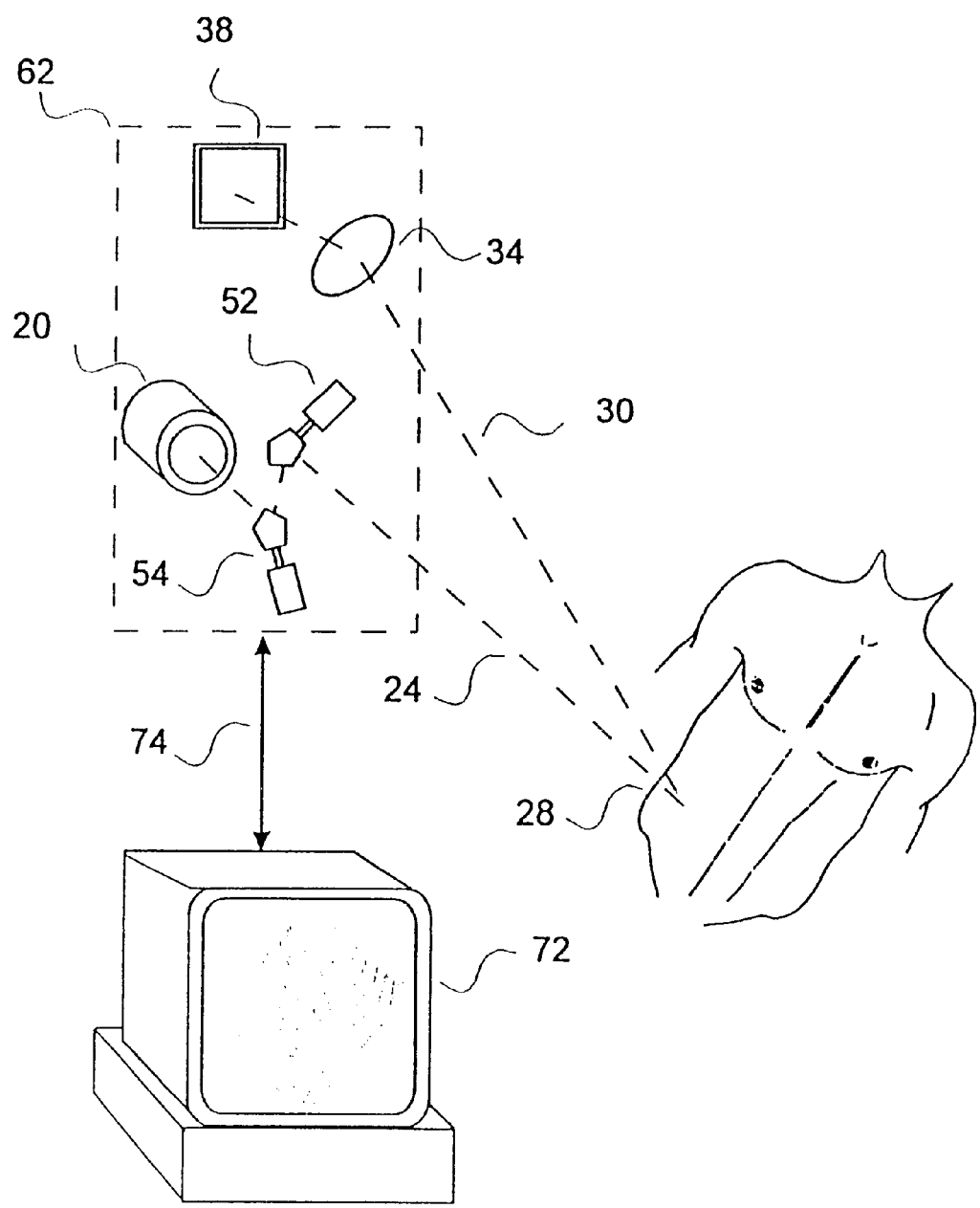
FIG. 2 is a diagram of a scanning arrangement to measure the motion of an anatomical object over a region-of-interest, comprising a source of illumination 20, focused by mirrors 52 and 54 on a two-axis scanner, controlled by a scanning controller which is itself controlled by a microcomputer 72. A beam 24 is produced which impinges on region-of-interest 28. The image propagates 30 though an optic 34 onto a position-sensitive-detector 38. Device 62 comprises the source of illumination 20, mirrors 52 and 54 on a two-axis scanner, the optic 34 and position-sensitive-detector 38. The microcomputer 72 is connected to the device 62 by electrical connections 74.

It has been shown that it is possible to obtained chest wall and lung volume measurements by optical reflectance motion analysis (8). These volume measurements are clinically very important, but cannot be obtained using a single point measurement of movement. The same arrangment is used as described above in the Examples, except that the device 62 for measuring movement incorporates a laser beam that is scanned over a user-selectable area on the body part. Referring to FIG. 2, the scanner consists of mirrors 52 and 54 on a two-axis scanner (General Scanning, Inc., Mass.) controlled by a scanning controller which is separate and is itself controlled by a microcomputer 72, or is incorporated within the microcomputer. The microcomputer 72, which is connected to the device 62 by electrical connections 74, can synchronize the scanner to position the laser beam as a user selectable location on the body part, whereupon the charge-coupled device array can b e interrogated to determine the position where the image of the laser spot impinged on the charge-coupled device array. Once the data is captured, the microcomputer causes the scanner to position the laser spot at a new location on the body part and the process is repeated. With this technique, it is possible to measure the movement of a large number of spots thus providing an accurate means with which to determine thoracoabdominal asynchrony, chest wall volume and lung volume. Optionally, if a position-sensitive-detector is used, a lock-in amplifier can be used to monitor the output of the position-sensitive-detector.

Figure 3:
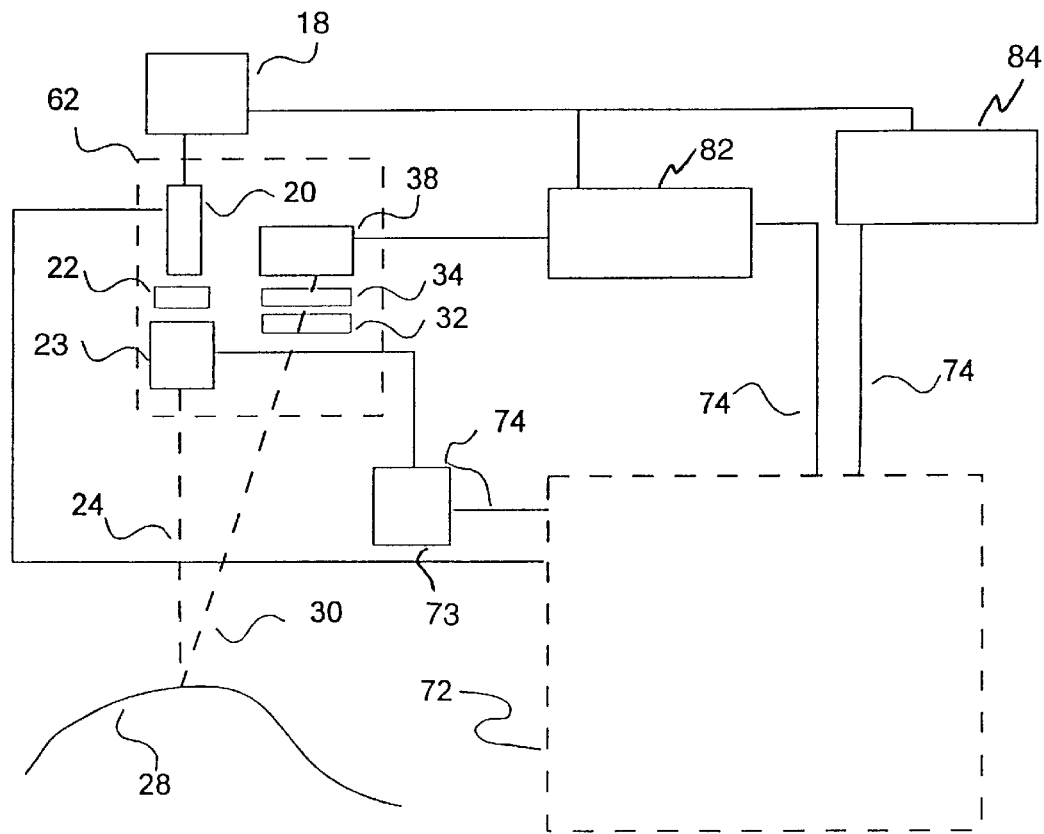
FIG. 3 is a schematic diagram of the scanning arrangement in FIG. 2. Output 24 of the source of illlumination 20 is collimated or focused with optic 22 and passes through a scanning device 23. The scanner is adjusted by an electronic controller 7 3 which is controlled by a computer 72. A bandpass filter 32, and focusing optic 34 capture the image 30 of the spot and project it onto the position-sensitivedetector 38. The output, if analog, of the position-sensitivedetector is captured by a lock-in amplifier 82, which receives a reference input from a waveform generator 84 which may or may not be incorporated in the microcomputer 72. The waveform generator also modulates the output of the illumination power supply 18, thus modulating the output of the illumination 20.

A schematic of the device is shown in FIG. 3, where the output 24 of the source of illlumination 20 is collimated or focused with optic 22 and passes through a scanning device 23, such as scanning mirrors or an electro-optical device such as a photoacoustic deflector. The scanner is adjusted by an electronic controller 73 which is controlled by a computer 72. A bandpass filter 32, and focusing optic 34 capture the image 30 of the spot and project it onto the position-sensitive-detector 38. The output, if analog, of the position-sensitive-detector is captured by a lock-in amplifier 82, which receives a reference input from a waveform generator 84 which may or may not be incorporated in the microcomputer 72. The waveform generator, which produces a sinusoidal voltage signal with a frequency selected by the user (between about 10 and 200 Hz), also modulates the output of the illumination power supply 18, thus modulating the output of the illumination 20.

EXAMPLE 8

An Arrangement with Two Projections of Incident Illumination

Figure 4:
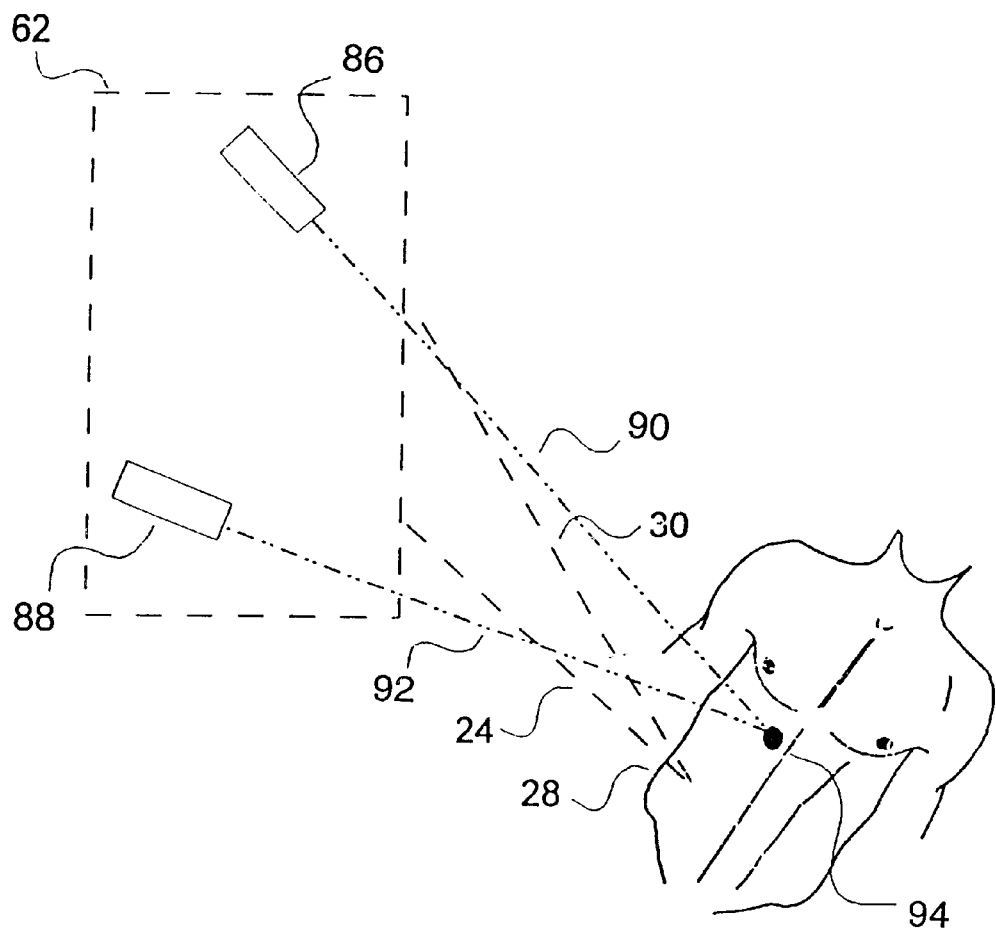
FIG. 4 is a diagram of an arrangement of two positioning lasers 86, 88 in a device 62 with the projection of incident illumination 90, 92 to position the anatomical target 94, which contains the region-of-interest (ROI) 28, at a known reference distance from the measuring device. The two beams can be arranged so that they coincide at a predetermined distance, or at a variable distance that may be determined from the angle of coincidence. This provides a means for calibrating the distance.

Another embodiment of the device that requires two projections of incident illumination, is shown in FIG. 4. The two beams can be arranged so that they coincide at a predetermined distance, or at a variable distance that may be determined from the angle of coincidence. This provides a means for calibrating the distance.

Here, two optical systems, which are nearly collinear, image the same point on the region of interest (either a structure already present, or a marker affixed). By altering the angle (p between the axes collinear with each imaging systems, and knowing the distance between the axes at the objective optic of each system, it is possible to match the two images at the detector and, when the two images coincide (determined usually by maximizing the contrast in the combined image, a process that can be automated), then a distance determination can be made. The angle of the adjusted optical system with respect to the fixed system is proportional to the target distance and can be calculated using simple geometry. Constant and rapid monitoring provides a measurement of movement. This arrangement is identical to that used in many 35mm single-lens reflex cameras and can be automated to provide information associated with rapid distance changes.

EXAMPLE 9

Portable Device for Measuring Movement of Thorax and Abdomen

Another device is of the portable hand-held device for measuring the movement of thorax and abdomen. In this case, the visible output of a super-luminescent light-emitting-diode (available from, for example, Marktech Optoelectronics Inc.) is collimated to produce a small spot at a distance of about 50 cm from the LED. The image of the spot is detector by a one-dimensional position-sensitive-detector. Another LED spot projector is configured collinearly with the imaging axis of the position-sensitive-detector. When the two spots produced by the two LEDs superpose on the anatomic region of interest, then knowing the geometry of the LEDs and imaging position-sensitive-detector, the distance between the anatomy and device, as well as the orientation, is optimal. The user initiates a measurement by pressing a trigger, which turns off the LED that is collinear with the position-sensitive-detector. The current from the position-sensitive-detector is monitored, amplified, digitized and presented visually to the user in the form of an LCD bargraph (Tandy Electronics Inc.), for example. The movement can be calculated as stated using a program in a microprocessor. The data can be captured with a small printer attached to the unit so that analysis can be done later. Optionally, the device may use a second LED for positioning whereby the beam projects from the top of the device and is used to calculate the distance between a fixed point (e.g. the ceiling) and the device. The total distance from the fixed point to the point to be measured is the variable to be measured, which is basically the additive distances calculated by both LEDs plus the length of the device. This mesurement eliminates error due to movement of the hand during the measurement process.

EXAMPLE 10

Devices to Monitor Sudden Infant Syndrome

Sudden infant death syndrome (SIDS) could be monitored by the following preferred embodiment of the device of the present invention. The device (SIDs monitor) makes use of a 2-D position-sensitive-detector which is coupled to wide-angle optics so as to image most of the infant as he/she sleeps in the crib. The orientation of the imager with the spot projection device is such that the baby is optimally positioned about 50 cm away from the SIDs monitor. The device itself could be attached to the side of the crib with a screw like device which provides for temporary attachment. The laser i n this case is a 0.2 mW visible diode laser (650 nm), the output of which is collimated and projected as a spot. What is important in this measurement is not an absolute determination of distance and change in distance, but a relative measurement of distance change. Therefore, the device is "calibrated" by first turning it on and capturing a sequence of measurements (current measurements at discrete times for perhaps 60 seconds) are captured and stored in memory. The mean and standard deviation of the measurements are calculated, and these values are then used with which to compare subsequent values to. Subsequent to the calibration, the device is set into "monitor" mode and whereupon it continually monitors movement (perhaps every second) and compares the result to the mean and standard deviation of the calibration. If, for a user selectable critical length of time (say 30 seconds), the movement is small enough such that the measurement falls two or three (user selectable) standard deviations below the calibration mean, and alarm is initiated. So called "fuzzy logic" analysis of the incoming data would be most suitable in this embodiment of the device.

EXAMPLE 11

Other Measurements for Clinical Uses

Other clinically useful measurements are possible using devices similar to those already described. For example, one may design a device to detect the rapid-eye-movements (REM) during REM sleep. In this case, the eyelids of the sleeping individual are known to move as the eyes move beneath them. To the external observer, the eye movements appear as a "wave" of motion or "bumps" moving across the eyelid. The same techniques described in the above embodiments may be applied to detect motion in the eyelids, and thereby create a useful means for evaluating REM sleep quantitatively.

The following references were cited herein.
Newacheck et al., Am J Public Health April 1998; 88(4): 610–617.
Taylor et al., Pediatrics November 1992;90(5): 657–662.
Ferrigno et al. J. Appl. Physiol. 77, 1224–1231, 1994.
Saumarez R C. J. Appl. Physiol. 60, 702–709, 1986.
Aubert et al. J. Biomed. Eng. 6, 134–140, 1984.
Kondo et al. Eur. Respir. J. 10, 1865–1869, 1997.
Cala et al. J. Appl. Physiol. 81, 2680–2689, 1996.
Cala et al. 1996. Ibid.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method for measuring body movement of a tissue of interest, comprising the steps of:
    emitting radiant energy to the surface of said tissue to form a spot;
    detecting an image of the pattern of radiant energy reflected from said spot, wherein said pattern corresponds to the position of said spot relative to the source of said radiant energy; and
    determining the change in said pattern with time, wherein the change in said pattern corresponds to the change of the position of said spot relative to said source of radiant energy, wherein said change of the position of said spot relative to said source of radiant energy indicates the body movement of said tissue.

2. The method of claim 1, wherein said radiant energy is produced by a source selected from the group consisting of a n incandescent light source, a fluorescent light source, a light-emitting diode, and a laser.

3. The method of claim 1, wherein said reflected radiant energy is detected by a device selected from the group consisting of a position sensitive detector, a charge-coupled device and a photodiode detector.

4. The method of claim 3, wherein said photodiode detector is accompanied by a reflective or transmissive mask.

5. The method of claim 1, wherein said tissue is selected from the group consisting of chest wall, lung, thorax, abdomen and eyes.

6. An apparatus for detecting movement of an anatomical structure, comprising:
    a source of radiant energy;
    a means for projecting said radiant energy in a pattern over a region of interest in said anatomical structure;
    an output optic for focusing said radiant energy onto said region of interest;
    a means for detecting change in said pattern of radiant energy reflected from said region of interest; and
    an imaging optic for focusing said reflected radiant energy onto said means of detection, wherein the distance between said region of interest and said output optic is determined by (i) the focal length of said imaging optic, (ii) the distance between said output optic and said imaging optic, and (iii) the position of the image of said pattern of radiant energy detected on said detector.

7. The apparatus of claim 6, wherein said source of radiant energy is selected from the group consisting of a n incandescent light source, a fluorescent light source, a light-emitting diode, and a laser.

8. The apparatus of claim 6, wherein said pattern is generated by a scanning device.

9. The apparatus of claim 8, wherein said scanning device is selected from the group consisting of scanning mirrors and electro-optical devices.

10. The apparatus of claim 9, wherein said electrooptical device is a photoacoustic deflector.

11. The apparatus of claim 8, wherein said pattern generated is composed of single or multiple spots.

12. The apparatus of claim 6, wherein said detector for detecting the pattern change is selected from the group consisting of a position-sensitive detector, a charge-coupled device and a photodiode detector.

13. The apparatus of claim 12, wherein said photodiode detector is accompanied by a reflective or transmissive mask.

14. A method of monitoring sudden infant death syndrome (SIDS) in an individual, comprising the steps of:
    attaching the apparatus of claim 6 to said individual; and
    monitoring the movement of said individual by detecting the change in the pattern of radiant energy reflected from said individual, wherein said movement reversely corresponds to the possibility of having a sudden infant death in said individual.

15. A method of evaluating rapid-eye-movement (REM) sleep in an individual in need of such evaluation, comprising the steps of:
    attaching the apparatus of claim 6 to said individual; and
    monitoring the movement in the eyelids of said individual by detecting the change in the pattern of radiant energy reflected from said eyelids, wherein said movement indicates the quality of REM sleep in said individual.

* * * * *